US012805897B2

(12) United States Patent
Lenker et al.

(10) Patent No.: US 12,805,897 B2
(45) **Date of Patent: *Nov. 24, 2026**

(54) STEERABLE ENDOLUMINAL PUNCH

(71) Applicant: Indian Wells Medical, Inc., Lake Forest, CA (US)

(72) Inventors: Jay A. Lenker, Lake Forest, CA (US); Scott Louis Pool, Laguna Hills, CA (US)

(73) Assignee: Indian Wells Medical, Inc., Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/967,428

(22) Filed: Dec. 3, 2024

(65) Prior Publication Data

US 2025/0090193 A1 Mar. 20, 2025

Related U.S. Application Data

(63) Continuation of application No. 17/981,151, filed on Nov. 4, 2022, now Pat. No. 12,156,675, which is a (Continued)

(51) Int. Cl.

*A61B 17/3205* (2006.01)
*A61B 17/00* (2006.01)

(Continued)

(52) U.S. Cl.

CPC .... *A61B 17/32053* (2013.01); *A61B 17/3417* (2013.01); *A61B 17/3478* (2013.01); *A61B 17/3496* (2013.01); *A61M 25/09041* (2013.01); *A61B 2017/00247* (2013.01); *A61B 2017/00309* (2013.01); *A61B 2017/00318* (2013.01);

(Continued)

(58) Field of Classification Search

CPC . A61B 17/34; A61B 17/3417; A61B 17/3478; A61B 17/3496; A61B 17/32053; A61B 2017/00309; A61B 2017/00318; A61B 2017/00247; A61M 29/00; A61M 25/0662; A61M 25/09041; A61M 25/065;

(Continued)

(56) References Cited

U.S. PATENT DOCUMENTS

| | | | |
|---|---|---|---|
| 3,802,440 | A | 4/1974 | Salem |
| 4,757,827 | A | 7/1988 | Buchbinder et al. |

(Continued)

FOREIGN PATENT DOCUMENTS

| | | |
|---|---|---|
| EP | 1898801 | 3/2008 |
| JP | 2004508147 | 3/2004 |

(Continued)

OTHER PUBLICATIONS

Examiner's Report and Examination Search Report from Canadian Patent Application No. 2,870,854 dated Nov. 7, 2019.

(Continued)

*Primary Examiner* — Shaun L David
*Assistant Examiner* — Cherie M Poland
(74) *Attorney, Agent, or Firm* — Crockett & Crockett, PC; K. David Crockett, Esq.

(57) ABSTRACT

A steerable transseptal punch system and method of using the steerable transseptal punch system to access the left atrium.

2 Claims, 16 Drawing Sheets

Related U.S. Application Data continuation of application No. 16/694,930, filed on Nov. 25, 2019, now Pat. No. 11,490,922, which is a continuation of application No. 15/625,868, filed on Jun. 16, 2017, now Pat. No. 10,485,569, which is a continuation of application No. 14/629,367, filed on Feb. 23, 2015, now Pat. No. 9,707,007, which is a continuation of application No. 13/750,689, filed on Jan. 25, 2013, now Pat. No. 8,961,550.

(60) Provisional application No. 61/663,517, filed on Jun. 22, 2012, provisional application No. 61/625,503, filed on Apr. 17, 2012.

(51) Int. Cl.

| | |
|---|---|
| ***A61B 17/34*** | (2006.01) |
| ***A61M 25/06*** | (2006.01) |
| ***A61M 25/09*** | (2006.01) |
| ***A61M 29/00*** | (2006.01) |

(52) U.S. Cl.
CPC .................. *A61M 25/0662* (2013.01); *A61M 2025/09116* (2013.01); *A61M 2025/09175* (2013.01); *A61M 29/00* (2013.01)

(58) Field of Classification Search
CPC ......... A61M 2025/09116; A61M 2025/09175; G05D 1/222
See application file for complete search history.

(56) References Cited

U.S. PATENT DOCUMENTS

| | | | | |
|---|---|---|---|---|
| 4,815,478 | A | 3/1989 | Buchbinder et al. | |
| 5,228,441 | A | 7/1993 | Lundquist | |
| 5,725,512 | A | 3/1998 | Swartz et al. | |
| 6,136,016 | A | 10/2000 | Barbut et al. | |
| 6,217,527 | B1 | 4/2001 | Selmon et al. | |
| 6,419,641 | B1 * | 7/2002 | Mark | A61B 10/0275 600/564 |
| 6,650,923 | B1 * | 11/2003 | Lesh | A61B 17/3478 600/407 |
| 6,685,679 | B2 | 2/2004 | Merdan | |
| 6,695,814 | B2 | 2/2004 | Greene et al. | |
| 6,749,560 | B1 * | 6/2004 | Konstorum | A61B 1/00071 604/525 |
| 7,471,697 | B2 | 12/2008 | Kamiya et al. | |
| 7,488,448 | B2 | 2/2009 | Wieting et al. | |
| 7,615,044 | B2 | 11/2009 | Scheibe | |
| 7,632,277 | B2 | 12/2009 | Woll | |
| 7,635,353 | B2 * | 12/2009 | Gurusamy | A61M 25/065 604/170.03 |
| 7,678,081 | B2 | 3/2010 | Whiting et al. | |
| 7,824,356 | B2 | 11/2010 | Wieting et al. | |
| 7,935,102 | B2 | 5/2011 | Breznock et al. | |
| 8,235,943 | B2 | 8/2012 | Breznock et al. | |
| 8,323,241 | B2 | 12/2012 | Salahieh et al. | |
| 8,480,606 | B2 | 7/2013 | Wieting et al. | |
| 8,491,619 | B2 | 7/2013 | Breznock | |
| 8,939,926 | B2 | 1/2015 | Wieting et al. | |
| 8,961,550 | B2 * | 2/2015 | Lenker | A61B 17/32053 604/164.01 |
| 9,445,836 | B2 | 9/2016 | Breznock | |
| 9,555,182 | B2 | 1/2017 | Wieting et al. | |
| 9,707,007 | B2 * | 7/2017 | Lenker | A61B 17/32053 |
| 9,993,266 | B2 | 6/2018 | Lenker et al. | |
| 10,016,210 | B2 | 7/2018 | Lenker et al. | |
| 10,016,221 | B2 | 7/2018 | Lenker et al. | |
| 10,034,686 | B2 | 7/2018 | Breznock | |
| 10,369,265 | B2 | 8/2019 | Wieting et al. | |
| 10,485,569 | B2 * | 11/2019 | Lenker | A61B 17/32053 |
| 10,485,579 | B2 | 11/2019 | Lenker | |
| 10,729,457 | B2 | 8/2020 | Lenker et al. | |
| 10,779,858 | B2 | 9/2020 | Lenker et al. | |
| 10,786,655 | B2 | 9/2020 | Lenker | |
| 10,806,483 | B2 | 10/2020 | Breznock | |
| 10,932,815 | B1 | 3/2021 | Lenker et al. | |
| 11,090,080 | B2 | 8/2021 | Lenker et al. | |
| 11,234,728 | B2 | 2/2022 | Lenker et al. | |
| 11,317,938 | B2 | 5/2022 | Lenker et al. | |
| 11,382,654 | B2 | 7/2022 | Lenker | |
| 11,490,922 | B2 * | 11/2022 | Lenker | A61B 17/32053 |
| 11,648,025 | B1 | 5/2023 | Lenker | |
| 11,771,463 | B2 | 10/2023 | Lenker | |
| 11,786,265 | B1 | 10/2023 | Lenker | |
| 11,819,642 | B2 | 11/2023 | Lenker | |
| 11,839,401 | B2 * | 12/2023 | Lenker | A61B 17/32053 |
| 11,844,548 | B1 | 12/2023 | Lenker | |
| 11,871,960 | B2 | 1/2024 | Lenker | |
| 11,911,066 | B2 | 2/2024 | Lenker | |
| 11,986,202 | B2 | 5/2024 | Lenker | |
| 12,156,675 | B2 * | 12/2024 | Lenker | A61M 25/09041 |
| 12,329,407 | B2 * | 6/2025 | Lenker | A61M 29/00 |
| 2004/0193073 | A1 | 9/2004 | DeMello et al. | |
| 2004/0267361 | A1 | 12/2004 | Donnelly et al. | |
| 2005/0004515 | A1 | 1/2005 | Hart et al. | |
| 2005/0101984 | A1 | 5/2005 | Chanduszko et al. | |
| 2005/0267495 | A1 | 12/2005 | Ginn et al. | |
| 2006/0074442 | A1 | 4/2006 | Noriega et al. | |
| 2006/0089637 | A1 * | 4/2006 | Werneth | A61B 18/16 606/41 |
| 2006/0252984 | A1 | 11/2006 | Rahdert | |
| 2007/0060878 | A1 | 3/2007 | Bonnette et al. | |
| 2008/0045863 | A1 | 2/2008 | Bakos | |
| 2008/0045908 | A1 | 2/2008 | Gould et al. | |
| 2008/0200980 | A1 | 8/2008 | Robin | |
| 2008/0243081 | A1 | 10/2008 | Nance | |
| 2009/0036832 | A1 | 2/2009 | Skujins et al. | |
| 2010/0185053 | A1 | 7/2010 | Hagen | |
| 2010/0228276 | A1 | 9/2010 | Breznock | |
| 2011/0093007 | A1 * | 4/2011 | Abbott | A61B 17/0644 606/213 |
| 2011/0184390 | A1 | 7/2011 | Zanni | |
| 2011/0245615 | A1 | 10/2011 | Iwasake et al. | |
| 2011/0245800 | A1 | 10/2011 | Kassab et al. | |
| 2011/0319905 | A1 | 12/2011 | Palme et al. | |
| 2012/0095434 | A1 | 4/2012 | Fung | |
| 2014/0343538 | A1 | 11/2014 | Lenker et al. | |
| 2015/0320437 | A1 | 11/2015 | Worrell et al. | |
| 2016/0235431 | A1 | 8/2016 | Brown | |
| 2016/0346519 | A1 | 12/2016 | Bagwell | |
| 2017/0105746 | A1 | 4/2017 | O'Keefe et al. | |
| 2017/0259041 | A1 | 9/2017 | Lenker | |
| 2018/0317949 | A1 | 11/2018 | Lenker et al. | |
| 2019/0008557 | A1 | 1/2019 | Lenker et al. | |
| 2019/0029750 | A1 | 1/2019 | Maini | |
| 2020/0163694 | A1 | 5/2020 | Lenker | |
| 2020/0246046 | A1 | 8/2020 | Gammie | |
| 2021/0068620 | A1 | 3/2021 | Walen et al. | |
| 2021/0353325 | A1 | 11/2021 | Fagan et al. | |
| 2021/0378648 | A1 | 12/2021 | Thissen et al. | |
| 2022/0339437 | A1 | 10/2022 | Sorajja | |
| 2022/0370121 | A1 | 11/2022 | Highsmith | |

FOREIGN PATENT DOCUMENTS

| | | |
|---|---|---|
| WO | WO9513752 | 5/1995 |
| WO | WO0064525 | 11/2000 |
| WO | WO2007-035497 | 3/2007 |
| WO | WO2007-115314 | 10/2007 |
| WO | WO2008069772 | 6/2008 |
| WO | WO2009112060 | 9/2009 |
| WO | WO2010151698 | 12/2010 |

OTHER PUBLICATIONS

Office Action dated Jul. 19, 2018 from European Patent Application No. 13861154.6.
International Search Report dated Jul. 18, 2013 from PCT Application PCT/US2013/034474.

(56) References Cited

OTHER PUBLICATIONS

Search Report dated May 16, 2013 from GB Application GB1308015.5.
International Search Report dated Mar. 6, 2014 from PCT Application PCT/US2013/073262.
Extended European Search Report dated Aug. 4, 2015 from EP Application 13778011.0.
Extended European Search Report dated Jun. 16, 2016 from European Patent Application 13861154.6.
Office Action dated Feb. 23, 2017 from Chinese Patent Application No. 201380072336.2.
Examination Report dated Oct. 6, 2017 from European Patent Application No. 13861154.6.
Notification of Reasons for Refusal dated Oct. 24, 2017 from Japanese Patent Application No. 2015545833.
International Search Report and Written Opinion dated Apr. 4, 2024 from IA PCT/US2023/037265.

* cited by examiner

STEERABLE ENDOLUMINAL PUNCH

This application is a continuation of U.S. application Ser. No. 17/981,151, filed Nov. 4, 2022, now U.S. Pat. No. 12,156,675, which is a continuation of U.S. application Ser. No. 16/694,930, filed Nov. 25, 2019, now U.S. Pat. No. 11,490,922, which is a continuation of U.S. application Ser. No. 15/625,868, filed Jun. 16, 2017, now U.S. Pat. No. 10,485,569, which is a continuation of U.S. application Ser. No. 14/629,367, filed Feb. 23, 2015, now U.S. Pat. No. 9,707,007, which is a continuation of U.S. application Ser. No. 13/750,689, filed Jan. 25, 2013, now U.S. Pat. No. 8,961,550, which claims priority to U.S. Provisional Application 61/663,517, filed Jun. 22, 2012 and U.S. Provisional Application 61/625,503, filed Apr. 17, 2012, both of which are hereby incorporated by reference in their entirety.

FIELD OF THE INVENTION

The invention relates to transseptal punches.

BACKGROUND OF THE INVENTION

Defects in the left atrium are common, and cause a variety of ailments, including atrial fibrillation, mitral valve prolapse, and atrial appendage thrombosis. These defects can be treated with minimally invasive procedures, with catheters inserted into the atrium. The left atrium must be approached from the right atrium, with catheters navigated through the vena cava and through the fossa ovalis, which is a thin wall between the right and left atrium. The fossa ovalis must be punctured to allow passage of catheters into the left atrium. To puncture the fossa ovalis, surgeons use a transseptal punch, which is also referred to as a Brockenbrough needle. The Brockenbrough needle is a long, very slender punch which is curved at its distal end. This curvature is important as it facilitates operation of the punch.

In a typical procedure in which access to the left atrium is obtained transseptally through the right atrium, a surgeon delivers a Mullins guide catheter into the right atrium, and then delivers a transseptal punch through the Mullins guide catheter to the right atrium. The transseptal punch (and usually an integral obturator or dilator) is navigated through the Mullins guide catheter with a stylet disposed within the punch. At this point the distal tip of the transseptal punch is disposed within the distal end of the Mullins guide catheter. After confirming that the punch is properly located and oriented, the surgeon then withdraws the stylet completely, and withdraws the Mullins guide catheter a short distance to expose the tip of the transseptal needle, and then pushes the transseptal punch through the fossa ovalis. After the transseptal punch has pierced the fossa ovalis and entered the left atrium, the surgeon pushes the Mullins guide catheter over the punch so that the distal tip of the Mullins guide catheter resided in the left atrium. The surgeon then removes the punch entirely from the Mullins guide catheter. After the Mullins guide catheter tip is disposed within the left atrium, the surgeon can deliver any desirable catheter or device to the left atrium through the Mullins guide catheter.

The transseptal punch, which is curved, is forced through the generally straight Mullins guide catheter. This may result in skiving or carving of small slivers of plastic from the inside of the Mullins catheter. Any slivers of plastic scraped from the catheter may be deposited in the right or left atrium, and subsequently cause injury to the patient.

SUMMARY OF THE INVENTIONS

The devices and methods described below provide for a robust steering mechanism for a steerable Brockenbrough needle, or transseptal punch. The transseptal punch comprises two tubes, one disposed within the other. The inner tube extends a short distance beyond the distal tip of the outer tube to provide the penetrating tip of the punch. The outer tube has a region of enhanced flexibility at its distal end, which establishes a deflectable or "steerable" segment. The inner tube is fixed to the outer tube at a point just distal to the deflectable segment. The inner tube, in a region corresponding to the deflectable segment, is split by a longitudinally extending slot. The deflectable segment can be forced to bend by pulling the inner tube proximally relative to the outer tube, (or pushing the outer tube relative to the inner tube). The longitudinally oriented slot in the inner tube provides flexibility needed for deflection, while preventing collapse of the outer tube. A proximal hub, which is fixed to both the inner tube and the outer tube, is operable to pull the inner tube distally relative to the outer tube (or push the outer tube relative to the inner tube). Use of the steerable transseptal punch avoids the skiving problems of prior art transseptal punches.

DETAILED DESCRIPTION OF THE INVENTION

Figure 1:
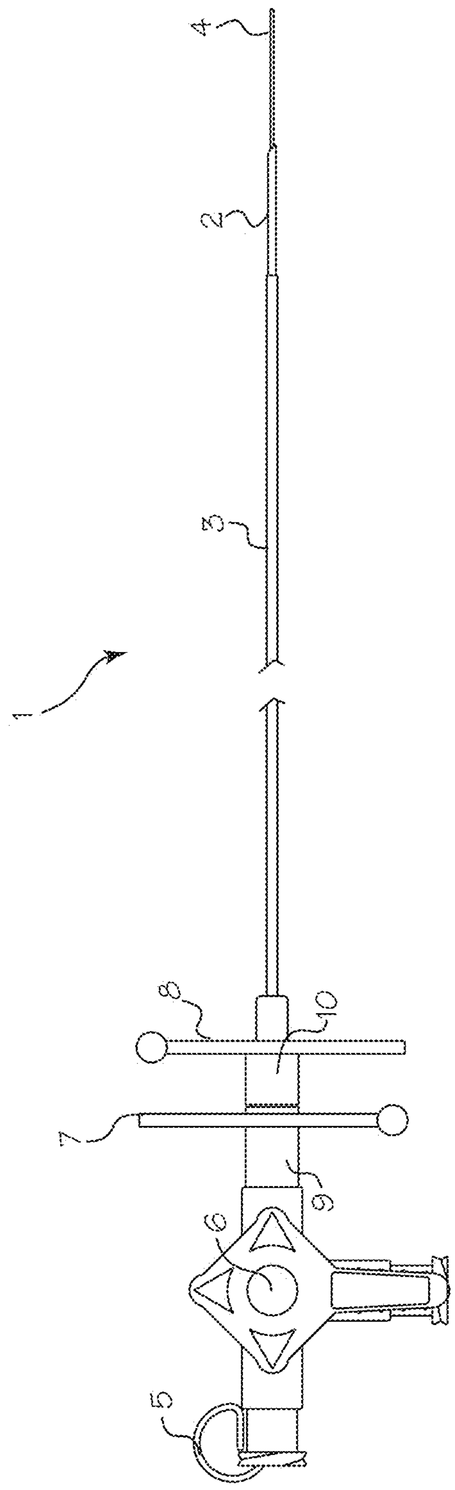
FIG. 1 illustrates a side view of a transseptal punch assembled so that the inner tube is bent in a direction 180 degrees opposite that of the outer tube, resulting in a substantially straight punch configuration.

FIG. 1 illustrates a side view of a punch, needle, or catheter assembly 1, with an integral articulating or bending mechanism which functions to bend the distal end of the punch. The punch assembly 1 comprises an inner tube 2, an outer tube 3, a stylet or obturator wire 4, an obturator grasping tab 5, a stopcock 6, an inner tube pointer 7, an outer tube pointer 8, an inner tube hub 9, and an outer tube hub 10. The distal end of the inner tube 2 is sharpened to serve as needle or a punch adapted to pierce the fossa ovalis. The stylet or obturator wire 4 is affixed to the obturator grasping tab 5. The stylet or obturator wire 4 is inserted through the central lumen of the inner tube 2 and is slidably disposed therein.

Figure 2:
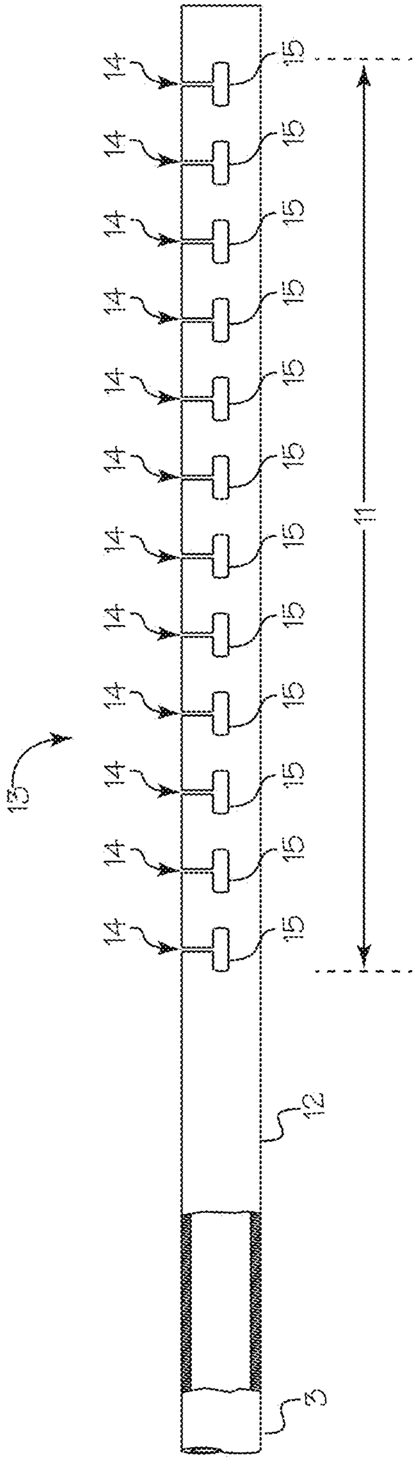
FIG. 2 illustrates a side, partial breakaway, view of an outer tube of an articulating transseptal punch comprising a plurality of slots near the distal end to generate a region of increased flexibility.

FIG. 2 illustrates a side view, in partial breakaway, of the distal end of the axially elongate outer tube 3, which has distal flexible portion 11, and a proximal, less flexible portion 12. The distal flexible portion is formed by a snake-cut portion 13 with a plurality of lateral or radial slots 14 cut into the tube, and a plurality of longitudinal slots 15 intersecting each radial slot on either side of the outer tube. The plurality of radial slots 14 serve to render the region of the outer tube 3 in which the radial slots 14 are located more flexible than the proximal region 12 which is not slotted. (The flexible portion may be rendered flexible, relative to the less flexible portion, by any means which weakens a length of the tube, which may include numerous longitudinal slots, piercings, a thinner wall thickness, etc. as well as the snake cuts depicted.) The plurality of longitudinal "T" cuts, serve to further render the region of the outer tube 3, in which the "T" cuts 15 reside, more flexible than in tubes where such "T" cuts 15 were not present. The longitudinal "T" cuts 15 are optional but are beneficial in increasing the flexibility of the outer tube 3 in the selected bend region. The radial slots 14 can be spaced apart by about 0.02 to about 1.0 inches with a preferred range of about 0.1 inches to about 0.8 inches and a further preferred range of about 0.15 inches to about 0.5 inches. The spacing between the partial lateral slots 14 can vary. The spacing between the radial slots toward the proximal end of the outer tube 3 can be about 0.3 inches while those radial slots 14 nearer the distal end of the outer tube 3 can be spaced about 0.15 inches apart. The spacing can change in a step function, it can change gradually moving from one end of the outer tube 3 to the other, or it can increase and decrease one or more times to generate certain specific flexibility characteristics. Increased spacing increases the minimum radius of curvature achievable by compression of the radial slots 14 while decreased spacing allows for a smaller minimum radius of curvature.

The number of radial slots 14 or, optionally, the number of radial slots 14 with longitudinal T-cuts 15 can number between about four and about 50 with a preferred number being between about six and about 25 and a more preferred number of about eight to about fifteen. As illustrated in FIG. 2, there are 12 radial slots 14, each modified with a "T" slot 15. The radial slots 14 can be shaped differently. For example, the radial slots 14 can be at angles other than 90 degrees to the longitudinal axis, curved, V-shaped, Z-shaped, W-shaped or the like. In other embodiments, the 'T' slots 15 can have, for example, further cuts approximately lateral to the longitudinal axis, along any portion of the "T" cut 15. In yet other embodiments, the distal flexible portion 11 can comprise a region of coil, helix or spring which can further comprise a backbone on one side.

The outer tube 3 can have an outer diameter of about 0.020 to about 0.1 inches with a preferred outside diameter of about 0.040 to about 0.060 inches and a more preferred diameter of about 0.045 inches to about 0.055 inches. In the illustrated embodiment, the outside diameter is about 0.048 inches while the inner diameter is about 0.036 inches. The inside diameter of the outer tube 3 can range from about 0.0.010 inches to about 0.090 inches.

Figure 3:
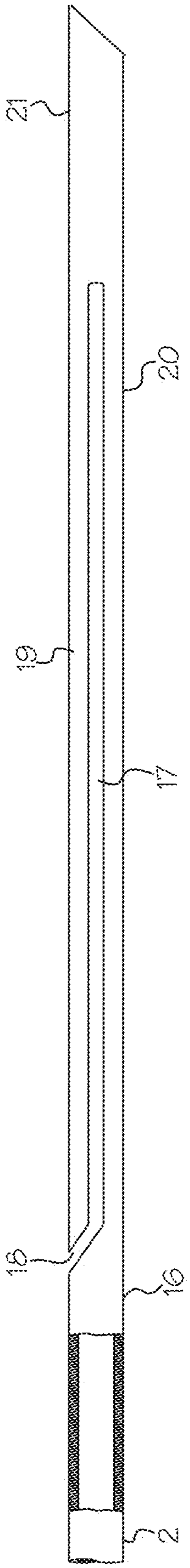
FIG. 3 illustrates a side, partial breakaway, view of an inner tube of an articulating transseptal punch comprising a longitudinal slot dividing the tube into two axially oriented parts which are connected at the distal end of the inner tube.

FIG. 3 illustrates the distal end of an axially elongate inner tube 2. The inner tube has a lumen running from the proximal end of the tube to the distal end of the tube, and comprises a proximal, uncut portion 16 (which, when assembled within the outer tube will reside within the proximal uncut region 12 of the outer tube), and a flexible region formed by a longitudinal slot 17. The slotted region is characterized by an angled lead-in slot 18, a pendent partial cylinder 19, a partial cylinder 20, and a distal uncut tip of the inner tube 21. The distal tip 21 interconnects the free side partial cylinder 19 and the partial cylinder 20, such that the partial cylinder 19 is attached to the remainder of the inner tube at its distal end. The connected side is a half-cylinder 20 spanning the intact proximal portion and the intact tube of the distal tip. The free side is a partial cylinder, pendent from the intact tube of the distal tip (though it could be pendent from the intact tube of the proximal portion), radially apposed to the partial cylinder 20. As described below, the pendent partial cylinder serves to limit the radial collapse of outer tube flexible portion during bending of the assembled punch, while the long slot provides the flexibility needed to allow deflection of the outer tube. The partial cylinder 19 and the partial cylinder 20 are most conveniently formed by cutting a slot in the inner tube, but can also be affixed to each other by welding, adhesives, fasteners, or the like.

The lead in 18 to the longitudinal slot 17 is beneficially angled to prevent guidewires, stylets, or other catheters, which are inserted through the central lumen from being caught or bumping against an edge. The angled lead in 18 serves as a guide to assist with traverse of a stylet, obturator, or guidewire past the lead in 18 and into the distal region of the steerable transseptal needle. The lead in 18 can be angled from between about −80 degrees (the angle can be retrograde) from the longitudinal axis (fully lateral) to about +2 degrees and preferably from about +5 degrees to about +20 degrees with a most preferred angle of about +8 degrees and about +15 degrees. In the illustrated embodiment, the angle of the lead in slot 18 is about 10 degrees from the longitudinal axis. A second feature of the lead in 18 is that it is positioned or located proximally to the most proximal "T" slot 15 in the outer tube 3 when the two tubes 3, 2 are affixed to each other (see FIG. 4). The lead in 18 may be located at least 1-cm proximal to the proximal most "T" slot 15 and preferably at least 2-cm proximal to the proximal most "T" slot 15 so that bending in the distal region does not distort the lead in 18 and cause kinking, misalignment, or pinching of the internal lumen.

The inner tube 2 can have an outside diameter that is slightly smaller than the inside diameter of the outer tube 3 so that the inner tube 2 can be constrained to move longitudinally or axially within the outer tube 3 in a smooth fashion with relatively little force exerted. In the illustrated embodiment, the outside diameter of the inner tube 2 is about 0.033 inches giving about a 0.0015 inch radial clearance between the two tubes 3 and 2. The inside diameter of the inner tube 2 can range from about 0.002 to about 0.015 inches less than the outside diameter of the inner tube 2. In the illustrated embodiment, the wall thickness of the inner tube is about 0.006 inches so the inside diameter of the inner tube is about 0.021 inches. The lumen of the inner tube 2 can be sized to slidably accept a stylet or obturator, as shown in FIG. 1. A typical stylet wire can range in diameter from about 0.01 to about 0.23 inches with a preferred diameter range of about 0.012 to about 0.021 inches. In another embodiment, the outer tube 3 has an outside diameter of about 0.050 inches and an inside diameter of about 0.038 inches. In this embodiment, the inner tube 2 has an outside diameter of about 0.036 inches and an inside diameter of about 0.023 inches. The radial wall clearance between the inner tube 3 and the outer tube 2 is about 0.001 inches and the diametric clearance is about 0.002 inches.

The inner tube 2 transmits force along its proximal non-slotted region 12 from the proximal end of the inner tube 2 to the lead in 18 where the force continues to be propagated along the connected side 20 to the distal end 21. The outer tube 3 transmits force along its proximal non-slotted region 12. Longitudinal forces applied to the distal, flexible region with the slots 14 cause deformation of the outer tube in an asymmetrical fashion with the side of the outer tube 3 comprising the partial lateral slots 14 forming an outer curve if the slots 14 are expanded and an inside curve if the slots 14 are compressed. Forces to cause bending are preferably exerted such that the partial lateral slots 14 are compressed up to the point where the gap closes, but no further, however forces can also be exerted to expand the slots 14, however limits on curvature are not in place because the lateral slots 14 can open in an unrestrained fashion except for the material properties of the outer tube 3.

The disconnected side 19 of the inner tube 2, separated from the connected side 20 by the longitudinal slot 17 and the lead in 18, serves to maintain an undistorted tube geometry and provide resistance to deformation while helping to maintain the inner lumen in a round configuration and provide a shoehorn or funnel effect to guide a guidewire, or stylet therethrough as they are advanced distally. The disconnected side 19, being separated from the force transmitting member 12 cannot provide any substantial longitudinal load bearing structure, although at its distal end, where it is integral or affixed to the distal end 21, some tension load carrying capability exists. The inner tube 2 can be considered a split tube and does not carry a load in compression or tension along substantially the entire length of the pendent side 19.

The radial slot 14 and the T-Slot 15 in the outer tube 3, as well as the longitudinal slot 17 in the inner tube 2, and the lead in slot 18 can be fabricated by methods such as, but not limited to, electron discharge machining (EDM), wire EDM, photoetching, etching, laser cutting, conventional milling, or the like. Different slot configurations can also be employed, such as curved slots, complex slots, zig-zag slots, or the like. The partial lateral slot 14 can be configured with a tongue and groove or dovetail design to prevent or minimize lateral movement or torqueing of the outer tube 3 in the flexible region. The tongue and groove or dovetail (not shown) can be generally centered between two "T" slots, for example. The parts can be ganged such that, using wire EDM, for example, a plurality of tubes can be cut to reduce manufacturing costs. As many as 20 to 30 tubes, or more, can be fixtured, secured, and etched by the aforementioned methods.

Figure 4:
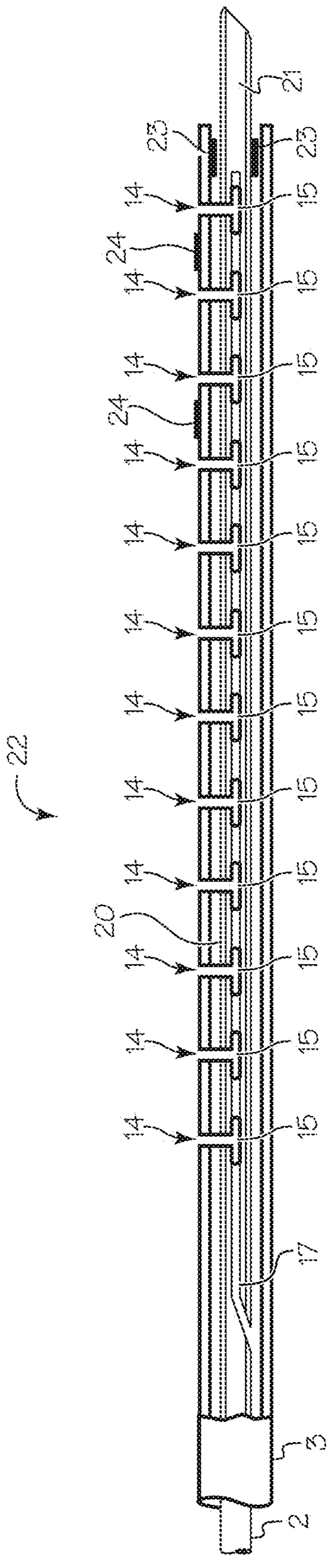
FIG. 4 illustrates a partial breakaway view of the distal end of the articulating transseptal punch comprising the outer tube and the inner tube arranged concentrically and oriented circumferentially.

FIG. 4 illustrates a side view of the distal end 22 of an articulating transseptal punch. The distal end 22 comprises the outer tubing 3 further comprising the radial slots 14 and the inner tube 2 further comprising the longitudinal slit 17 and the distal tip 21. A weld 23 affixes the distal end of the outer tubing 3 to the connected side 20 of the inner tube. This weld is preferably a ring weld circumscribing substantially the entire circumference of inner tube. The outer tube 3 and the inner tube 2 are rotationally oriented about the longitudinal axis such that the connected side 20 of the inner tube 2 is generally aligned with, and affixed or welded at weld 23 to the outer tubing 3 on the side comprising the partial lateral slits 14. In other words, the slots and the connected side are circumferentially aligned, meaning that they are positioned at or near the same line along the circumference of the tubes. Weld 23 may be spot weld, which fixes only a small portion of the circumference of the outer tube to a corresponding small portion of the circumference of the inner tube. In this case, the slots and the fixation point between the outer tube and the inner tube are circumferentially aligned, meaning that they are positioned at or near the same point along the circumference of the tubes. The width of the partial lateral slits 14, the T-slots 15, and the longitudinal slot 17 can range from about 0.001 to about 0.050 inches with a preferred range of about 0.005 to about 0.020 inches. In the device shown in FIG. 4, adapted for use as a transseptal punch to be used within a Mullins catheter, the slits 14, 15, and 17 are about 0.010 inches. The width of the partial lateral slits 14 on the outer tube 3 can be used, in compression to provide at least some limit to how much the outer tube 3 can bend in compression along the side comprising the partial lateral slits 14. Note that the distal end of the inner tube 2 extends beyond the distal end of the outer tube 3. The inner tube 2 extends about 10 mm to about 20 mm or more beyond the distal end of the outer tube 3. The distal end 22 can further comprise one or more separate radiopaque markers 24. This construction provides for reduced device complexity, increased reliability of operation, and reduced manufacturing costs relative to other steerable devices. The system also provides for high stiffness when the distal end 22 is straight, as illustrated, curved as in FIG. 5, or curved, bent, deflected, steered, or otherwise deformed in any configuration between straight and maximally curved. The articulating transseptal punch is necessarily stiff, has high column strength, and has significant resistance to bending from external sources because it needs to force an incision through tissue at the end of a very long, 2 to 4 foot length, of very small diameter punch tubing. Thus, the all-metal tubing punch can translate forces from its proximal end to its distal end that a substantially polymeric catheter could not come close to equaling. Catheters carrying such a punch would be less effective for the specific purpose of transseptal puncturing than would the articulating transseptal needle.

The distal end 22 of the articulating transseptal punch is generally fabricated from metals with sufficient radiopacity or radio-denseness that they are clearly visible under fluoroscopic or X-ray imaging. However, if this is not the case, additional radiopaque markers 24 can be affixed to the outer tube 3, the inner tube 2, or both. These radiopaque markers can comprise materials such as, but not limited to, tantalum, gold, platinum, platinum iridium, barium or bismuth compounds, or the like.

Close tolerances between the internal diameter of the outer tube 3 and the outside diameter of the inner tube 2, ranging from a radial gap of between about 0.0005 inches to about 0.008 inches, depending on diameter, cause the two tubes 3 and 2 to work together to remain substantially round in cross-section and not be ovalized, bent, kinked, or otherwise deformed. The two tubes 3 and 2 can be fabricated from the same materials or the materials can be different for each tube 3, 2. Materials suitable for tube fabrication include, but are not limited to, stainless steel, nitinol, cobalt nickel alloy, titanium, and the like. Certain very stiff polymers may also be suitable for fabricating the tubes 3, 2 including, but not limited to, polyester, polyimide, polyamide, polyether ether ketone (PEEK), and the like. The relationship between the inner tube 2, the outer tube 3, and the slots 14, 15, 17, 18 serve to allow flexibility and shaping in high modulus materials such as those listed above, which are not normally suitable for flexibility. The internal and external surface finishes on these tubes 3, 2 are preferably polished or very smooth to reduce sliding friction between the two tubes 3, 2 because of their very small cross-sections and their relatively long lengths. Lubricants such as, but not limited to, silicone oil, hydrophilic hydrogels, hydrophilic polyurethane materials, PFA, FEP, or polytetrafluoroethylene (PTFE) coatings can be applied to the inner diameter of the outer tube 3, the outer diameter of the inner tube 2, or both, to decrease sliding friction to facilitate longitudinal relative travel between the two tubes which is necessary for articulating the flexible, slotted region near the distal end 22 of the articulating transseptal sheath. The exterior surface of the outer tube 3 can be covered with a polymeric layer, either substantially elastomeric or not, which can cover the slots 14, 15, etc. and present a smoother exterior surface to the environment. The exterior surface can be affixed or configured to slip or slide over the exterior of the outer tube 3.

The inner tube 2 may be split lengthwise in the flexible region, and a portion, or the entirety, of the distal end of the inner tube 2 can be affixed to the outer tube 3 and functionality can be retained. The distal end 21 of the inner tube 2 can, in some embodiments, be retained so as to create a cylindrical distal region 21 in the inner tube 2 and this entire cylindrical distal region 21, or a portion thereof that does not project distally of the distal end of the outer tube 3 can be welded to the outer tube 3 around a portion, or the entirety of the circumference of the outer tube 3. If only a portion of the inner tube 2 is welded to the outer tube 3, then the weld is beneficially located, approximately centered, on the side of the outer tube 3 comprising the partial lateral slots 14. The cylindrical distal region 21 is a beneficial construction, rather than completely cutting the inner tube 2 away on one side, since the distal region 21 projects distally of the distal end of the outer tube 3 to form the tip of the punch further comprising a sharpened tip 25 configured to punch through myocardial tissue (refer to FIGS. 11 and 13).

Figure 5:
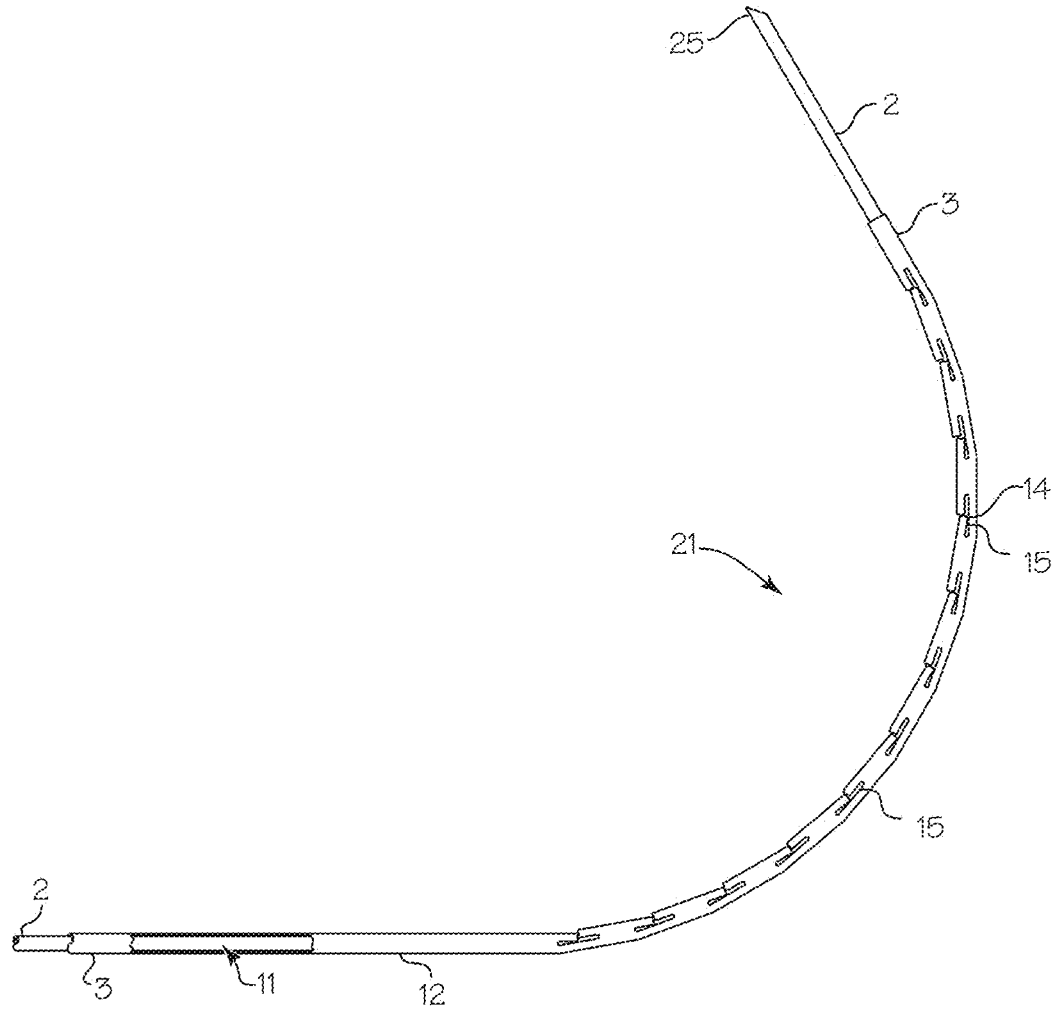
FIG. 5 illustrates a side view of the distal end of the articulating transseptal punch incorporating the inner split tube and the outer T-slotted tube with the inner tube being pulled proximally relative to the outer tube causing the outer tube to deform into a curve having very stiff, or rigid, mechanical properties.

FIG. 5 illustrates the distal end 22 of the articulating transseptal needle in a curved configuration. This view shows the distal end 22, the outer tube 3, the inner tube 2, the outer tube lumen 11, the distal end of the proximal region of outer tube 12, the distal end 21 of the inner tube 2 the sharpened distal tip 25, the plurality of outer tube longitudinal cuts or slots 15, and the plurality of outer tube partial lateral cuts 14. The outer tube partial lateral cuts 14 provide spaces that close up when the side of the tube in which the lateral cuts 14 are located is placed in compression. Such compression is generated by pushing the outer tube 3 distally relative to the inner tube 2, or, conversely, pulling the inner tube proximally relative to the outer tube, through operation a proximally located translating mechanism. When the gaps of the partial lateral cuts 14 close, further compression is much more difficult because the outer tube 3 stiffens substantially when no further gap exists for compression. The composite structure, with the inner tube 2 nested concentrically inside the outer tube 3, is relatively stiff and resistant to kinking no matter what amount of curvature is being generated. Such stiffness is essential when using the articulating transseptal needle to deflect another catheter such as a Mullins introducer, or other guide catheter.

Preferred radius of curvatures for the distal end can range from about 1 inch to about 6 inches, with a preferred range of about 2 inches to about 4 inches and a more preferred range of about 2.5 to about 3.5 inches for the purpose of puncturing the atrial septum. Even smaller radius of curvatures would be appropriate in, for example, the cerebrovasculature, the arteries of the heart, and the like. The radius of curvature need not be constant. The proximal end of the flexible region can have the partial lateral cuts spaced more widely than those at the distal end of the flexible region, causing the distal end to bend into a tighter radius than, the proximal end of the flexible region. In other embodiments, the distal region can be less flexible than the proximal end of the flexible region.

The partial lateral cuts 14, and the "T"-slots in the outer tube 3 are beneficially treated using etching, electropolishing, passivation, sanding, deburring, machining, or other process to round the external edges of the partial lateral cuts 14. Thus, the edges are blunted or rounded so they are not sharp such as to cause the articulating transseptal needle to dig, skive, or shave material from the inside of a polymer guide catheter since that is a benefit of using the articulating transseptal needle rather than a pre-curved, non-articulating, transseptal needle or other punch that, when advanced distally through a polymeric sheath, can scrape or skive material from the inner diameter of the sheath or introducer.

The distal end 25 is preferably sharp, but it can also be somewhat or completely blunted. In the case of partially or completely blunted distal construction, the distal end can be operably connected to a source of electrical or radiofrequency (RF) energy and puncture holes can be created using the electrical or RF energy. The energy is carried by the inner tube 2, which is preferably electrically insulated from the outer tube 3, from the hub 49 into which electrical or RF energy can be applied to the distal tip 25.

Figure 6:
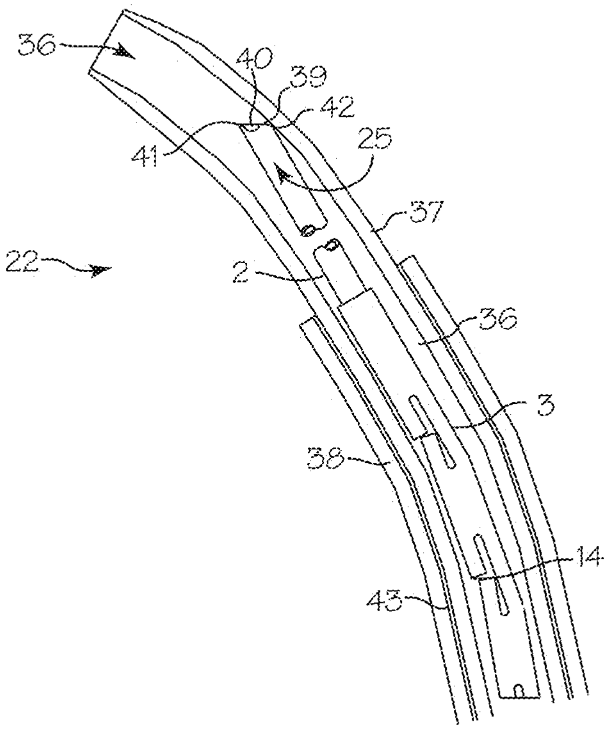
FIG. 6 illustrates the distal end of an articulating septal punch advanced nearly to the distal end of an obturator or dilator, which is coaxially, removably assembled into the central lumen of a guide catheter sheath.
Figure 7:
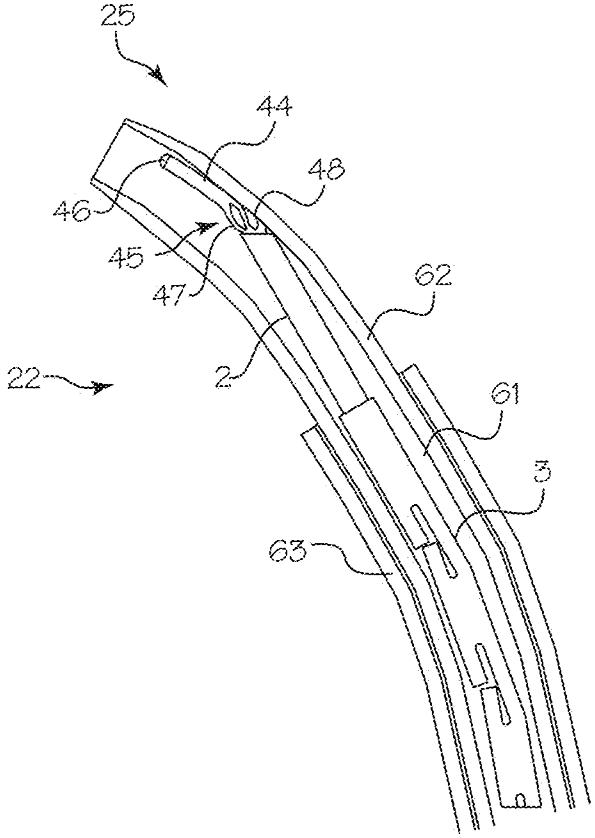
FIG. 7 illustrates the distal end of an articulating transseptal punch further comprising a removable obturator having a collapsible distal shield.

FIGS. 6 and 7 illustrate the distal end 22 of the articulating transseptal punch advanced through a central lumen 36 of a dilator or obturator 37, which in turn is disposed within a Mullins guide catheter 38. The distal end 22 comprises the outer tube 3, comprising the plurality of partial lateral cuts 14, and the inner tube 2, comprising a sharpened distal tip 25. The sharpened distal tip 25 comprises a bevel 39, one or more facets 40, a point 41, and a rounded or blunted outside edge 42. The obturator 37 further comprises the central lumen 36. The guide catheter 38 further comprises a central lumen 43. The guide catheter 38 and its obturator 37 are generally curved near the distal end. When the distal end 22 of the transseptal punch is advanced distally through the lumen 36 of the obturator 37, scraping of the inner wall of the obturator 37 is prevented by inclusion of a rounded edge 42 of the distal end 25 toward the outside of the curvature. The distal sharp end 25 comprises a bevel 39 to create a sharpened tissue punch with a point 41. As illustrated, the point 41 of the bevel is radially aligned with the side of the punch with the slots 14 and the pendent partial cylinder 19. The facets 40 are optional but can be provided in numbers ranging from one to about 10. The bevel 39 can be generated at a single angle, or with a complex curvature. In some embodiments, the bevel 39 can be generated at an angle of about 20 to about 80 degrees from lateral to the axis of the tube with a preferred range of about 30 to about 60 degrees from lateral, and a most preferred range of about 40 to about 50 degrees. The point 41 can be a point in three dimensions or in two dimensions, such as the point 41 illustrated herein.

FIG. 7 illustrates the distal end 22 of an articulating transseptal punch further comprising a stylet 4. The stylet comprises the core wire 44, a proximal lock and grasping tab 5 (shown in FIG. 1), a self-expanding basket 45, and the rounded distal tip 46. The basket is constrained in a small diameter configuration when withdrawn into the inner tube 2, and expands resiliently or pseudoelastically to a large diameter configuration when pushed distally out of the inner tube. The large diameter configuration has a diameter large enough to block the sharp distal tip of the inner tube from scraping against the inner wall of the obturator 37 or guide catheter 38. With the basket formed on the distal end of the stylet, the stylet 4 acts as a shield to assist with blunting the sharpened distal end. The stylet 4 can be fabricated from materials such as, but not limited to, stainless steel, nitinol, cobalt nickel alloy, titanium, and the like using methods such as cold rolling or tempering to achieve substantial spring conditions. The collapsing shield feature 45 is created by means of a split tube of spring stainless steel or pseudoelastic nitinol, comprising a plurality of longitudinal extending struts 47 defined by longitudinally extending slots or openings 48. The struts are biased outward to create a radially bulging basket structure when unrestrained, which can be readily deformed to a small diameter configuration which fits inside the lumen of the inner tube when inserted into the lumen. The slotted tube shield 45 is preferably integral to the core wire 44, but may be disposed as a separate structure over the core wire. The amount of outward bulge (the outer diameter in the large diameter, unconstrained configuration) of the shield 45 need not be large but must be sufficient interfere with contact between the sharp distal tip of the inner tube and the inner wall of the surrounding catheter component. The basket in the large diameter configuration need only be larger than the inner diameter of the inner tube, but preferably equals or exceeds the inner diameter of the inner tube. The benefits of the stylet and basket, combined with the hollow Brockenbrough needle, may be obtained with or without the steerable Brockenbrough structure described in the other figures. Additionally, the stylet can be replaced with a guide wire, with self-expanding basket disposed on the distal end of the guide wire, as described in relation to the stylet. The expandable distal end of the stylet is beneficial because the relatively large wall thickness of the inner tube (about 0.004 to 0.009 inches) relative to the ID (about 0.013 to 0.023 inches) may not adequately protect the sharp distal end of the inner tube from damaging the interior of a catheter, even with a non-expandable stylet in place and projecting distally therefrom. The expandable distal end of the stylet can be forced open and closed, if comprised of a non-elastic or non-superelastic material rather than a self-expanding material.

The outer tube 3 can be modified to adjust stiffness. It can be preferential to increase the resistance to bending moving distally to proximally on the outer tube 3. This increase in bending resistance contravenes the tendency of the outer tube to bend more severely at the proximal end of the flexible region than in the distal region. It is possible to configure the bending so that the bend radius is approximately constant or such that a greater curvature (smaller radius of bending) is generated moving toward the distal end of the bendable region. The partial lateral slots 14 can be cut with reduced depth more proximally to increase the resistance to bending imparted by the outer tube 3. The partial lateral slots 14 can be cut more narrowly in the more proximal regions to reduce the distance the slot 14 can close. The T-slots 15 can be reduced in length or removed in the more proximal regions of the flexible region of the outer tube 3. Elastomeric bumpers or fillers can be added to some of the partial lateral slots 14 to reduce the amount the partial lateral slots 14 can compress. Once the partial lateral slots 14, associated with the T-slots 15 have closed under bending of the outer tube 3, further bending is resisted and is substantially arrested. By tailoring the width and spacing of the partial lateral slots 14, a specific final curvature can be tailored for a given catheter.

Figure 8:
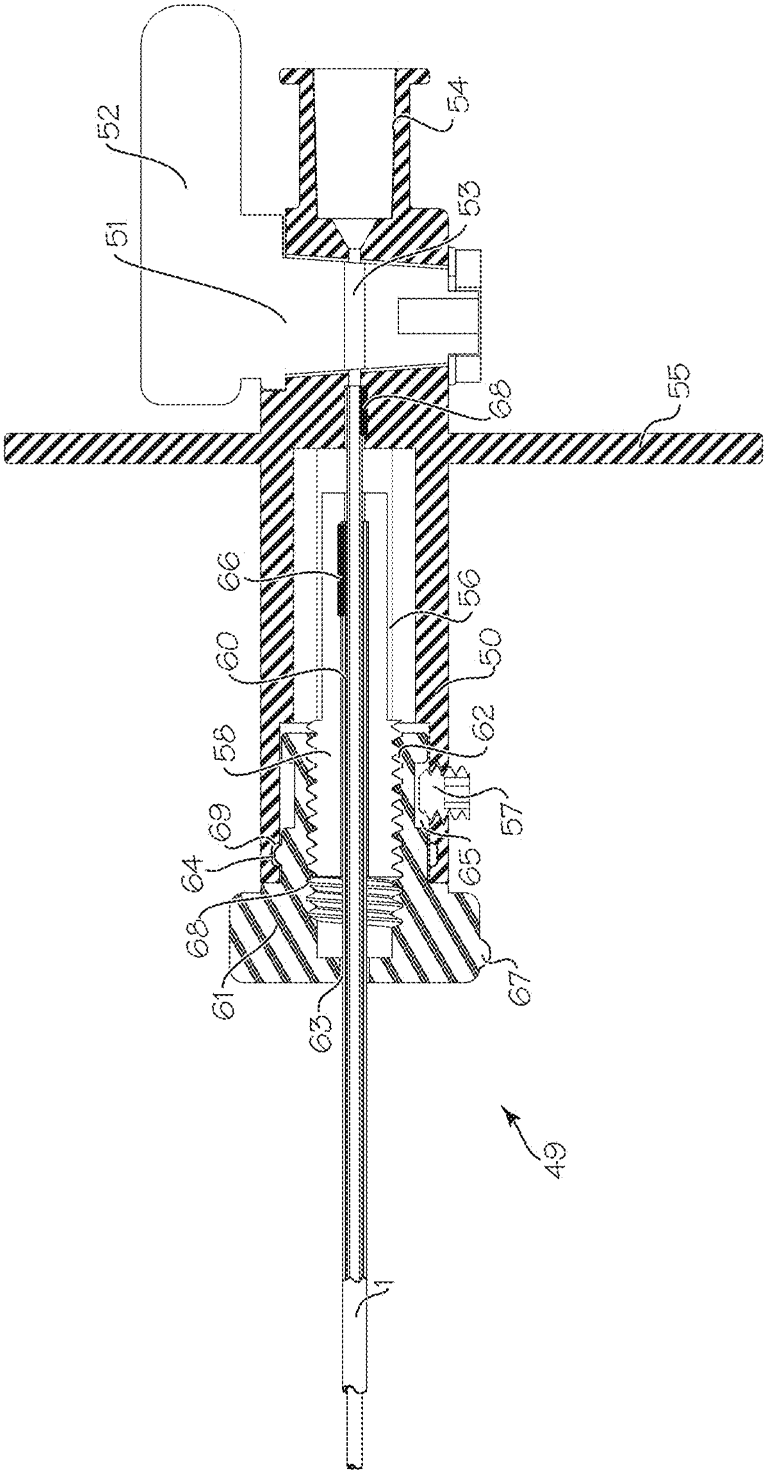
FIG. 8 illustrates a cross-sectional view of the proximal end of the articulating transseptal punch comprising a stopcock and a bend adjusting mechanism.

FIG. 8 illustrates a side, cross-sectional view of the hub 49 of an articulating septal punch. The hub 49, disposed at the proximal end of the outer tube 2 and the inner tube 2, includes a hub body 50, a stopcock petcock 51 further comprising a petcock handle 52 and a petcock through bore 53, a Luer lock fitting 54, an arrow pointer 55, a keyed lumen 56, a setscrew or pin 57, a jackscrew body 58 further comprising a plurality of threads 59 and a central lumen 60, a control knob 61 further comprising a plurality of threads 62, a central lumen 63, the protrusion 64, and a circumferential recess 65, an outer tube weld 66, an orientation mark 67, and an inner tube weld 68. The hub body 50 can further comprise a plurality of recesses or complementary structures 69. The petcock 51 is affixed to the petcock handle 52 by welding, integral fabrication, fasteners, adhesives, or the like. The petcock 51 is retained within a lateral through bore in the hub body 50, which is in the illustrated embodiment, tapered, using a locking “C” washer, fastener, screw, pin, or the like (not shown). The petcock 51 can be rotated about its longitudinal axis to align the through bore 53 with the axis and central lumen of the hub body 50 or it can be rotated sideways to shut off and seal the lumen against the flow of fluids. The Luer lock 54 can be affixed to, or integrally fabricated with, the hub body 50. The knob 61 is retained within the hub body 50 by the setscrew of pin 57 which prevents axial movement but permits rotational movement as constrained by the setscrew, projection, or pin 57 riding within the circumferential recess 65 which is integrally formed or affixed to the knob 61. The jackscrew body 58 is capable of axial movement within the hub body 50 but is restrained from rotation about the long axis by flats or features on the exterior of the jackscrew body 58 which are constrained by flats or features in the keyed lumen 56. The knob 61 comprises threads on its internal lumen which engage with external threads 62 on the jackscrew body 58. Rotation of the knob 61 thus causes the jackscrew body 58 to move axially proximally or distally with mechanical advantage. Rotation of the knob 61 can be forced using manual action or using a motor or other mechanism (not shown). The outer tube 3 is affixed to the jackscrew body 58 by the outer tube weld 66. The inner tube 2 is affixed to the hub body 50 by the inner tube weld 68. The central lumen of the inner tube 2 is operably connected to a central lumen of the hub body 50, the petcock through bore 53, and the lumen of the Luer fitting 54.

The knob 61 can comprise markings 67 to permit the user to visualize its rotary or circumferential position with respect to the hub body 50. These markings 67 can comprise structures such as, but not limited to, printed alphanumeric characters (not shown), a plurality of geometric shapes such as dots, squares, or the like, or the markings can comprise raised or depressed (embossed) characters of similar configuration as described for the printed markings. In an embodiment, the knob 61 can comprise a number on each of the facets so the facets can be numbered from one to 6, in the illustrated embodiment. The knob markings 67 can further comprise raised structures, as illustrated, which can further be enhanced with contrasting colors for easy visualization.

The knob 61 can further comprise one or more complementary structures affixed or integral thereto, such as a plurality of protrusions 64 that fit into detents 65 affixed or integral to the proximal end of the hub body 50. Such protrusions extending into detents in the hub body 50 can provide a ratcheting or clicking sound as well as providing resistance to inadvertent movement of the knob 61 once it is rotated to the correct location. The knob 61, in some embodiments, can be biased toward the hub body 50 to ensure that complementary structures such as the protrusions and detents come into correct contact. In other embodiments, the knob 61 can comprise a ratchet system to further control its rotary movement with respect to the hub body 50. In other embodiments, the knob 61 can comprise one or more detents (not shown) while the hub body 50 can comprise one or more complementary protrusions (not shown). It is beneficial that the knob 61 be moved only when required by the user and not by accident or not when it is required to maintain its rotary position and, by consequence, the curvature at the distal end of the tubing. The number of ratchet locations, or low energy positions or set points, can range from about 2 per 360 degree rotation to about 20 with a preferred number of ratchet locations ranging from about 4 to about 12.

Figure 9:
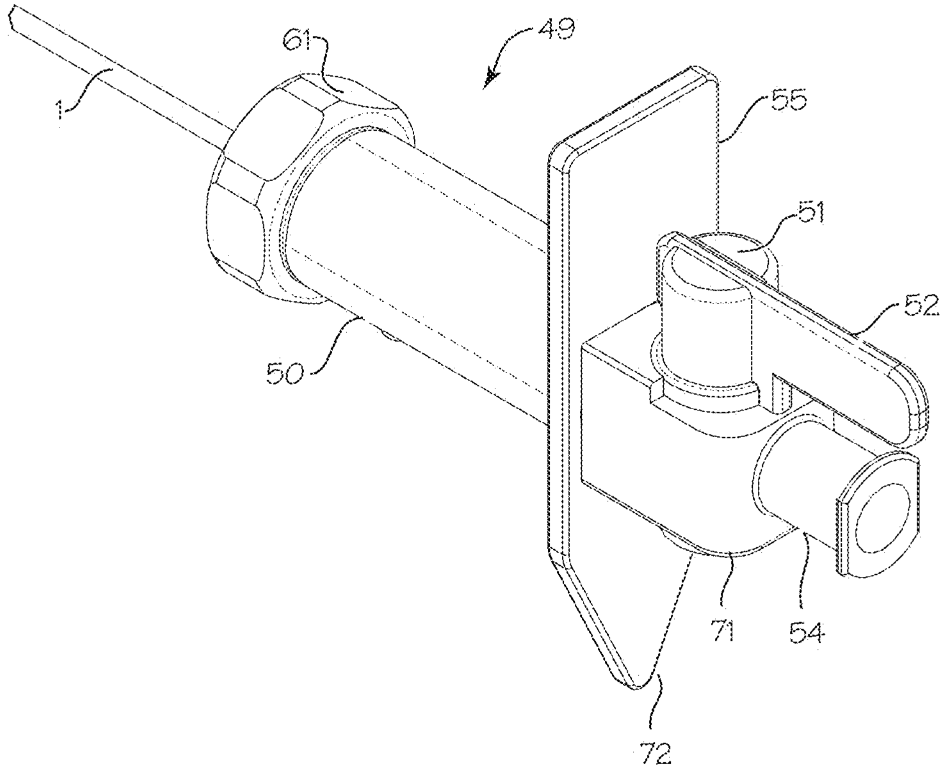
FIG. 9 illustrates an oblique view of the proximal end of the articulating transseptal punch.

FIG. 9 is a perspective view of the proximal steering mechanism of FIG. 8, showing the steering hub 49 of the steerable transseptal needle, including components used to steer the needle. The proximal hub includes the knob 61, the hub body 50, the arrow pointer further comprising the pointer 70, a stopcock body 71, the petcock 51, the petcock handle 52, and the Luer fitting 54. The pointed end 72 is aligned with the point of the bevel of the needle (and the direction of the curvature of the needle), and provides a landmark by which the surgeon can determine the orientation of the bevel point within the Mullins catheter.

Figure 10:
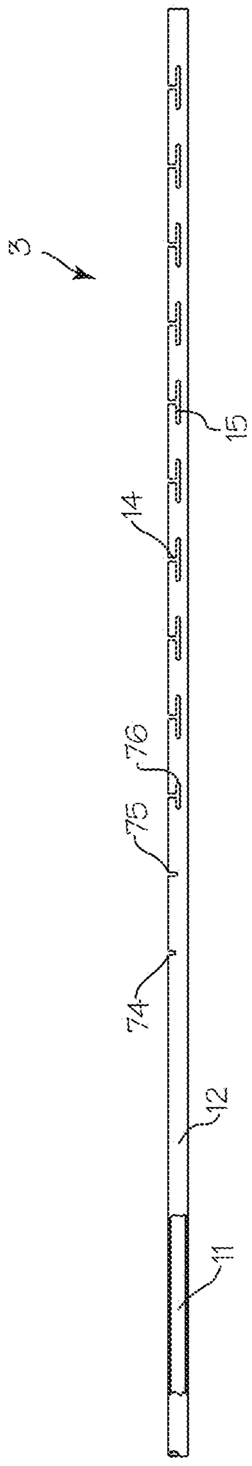
FIG. 10 illustrates an outer tube cut in its flexible regions with shorter lateral slots and with reduced or complete elimination of some T-slots near the proximal end of the flexible region to improve resistance to bending in that region.
Figure 11:
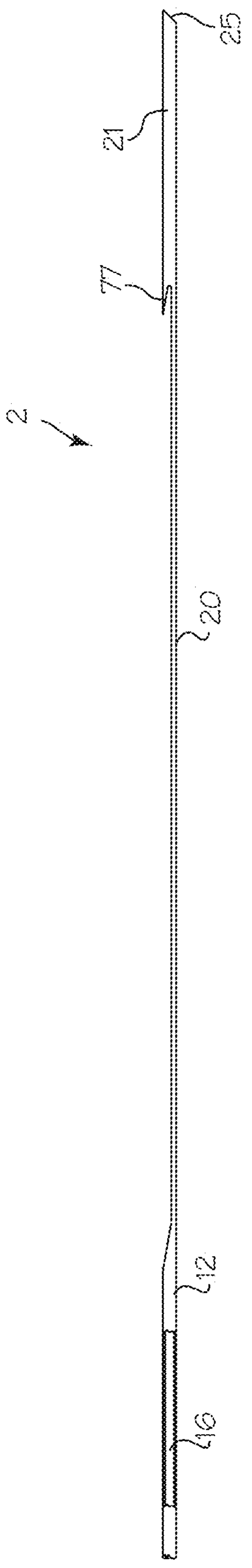
FIG. 11 illustrates an inner tube wherein the disconnected side has been removed, leaving only the connected side and the distal end.

FIGS. 10 and 11 illustrate alternative embodiments for the outer tube and inner tube. FIG. 10 illustrates the outer tube 3 comprising the lumen 11, the proximal tube wall 12, the plurality of partial lateral slots 14, the plurality of T-slots 15, a short partial lateral slot 73, a slightly longer partial lateral slot 74, and a standard length lateral slot 14 but with a shortened T-slot 75. The most proximal partial lateral slot 73 penetrates less than the standard partial lateral slots 14. The second (moving distally) partial lateral slot 74 is slightly longer than slot 73 and therefore is more flexible in that region and requires less force to generate bending. The third partial lateral slot comprises the shortened T-slot 75 which reduces the ability of the tubing to bend given a constant bending force.

FIG. 11 illustrates the inner tube 2 comprising the lumen, the proximal region 12, the connected side 20, the distal end 21, the sharpened tip 25, and a beveled lead-in 76 at the proximal end of the distal end 21. The extended half-pipe region 77 extends substantially the entire length of the snake cut region of the outer tube, and may extend at least as long, along the length of the device, as the snake cut region. As illustrated, the half-pipe region starts just proximal to the snake cut region of the outer tube, and ends distally at a point just distal to the snake cut region and just proximal to the weld affixing the inner tube to the outer tube. The open side of the half pipe region is on the same side of the device as the T-slots of the snake cut region (that is, the open side of the half pipe region is circumferentially aligned with the T-slots). The proximal end of the disconnected region can be moved distally to increase the stiffness of the inner tube 2 in a specific region, generally the most proximal part of this distal, flexible region.

Since, during use of the steerable transseptal needle, the needle is advanced distally through an already placed Mullins guide catheter, it is beneficial that the straight steerable transseptal needle be capable of advancing through any curvatures in the already placed introducer, sheath, or guide catheter. Thus, in certain embodiments, the bevel is oriented such that the pointed point of the sharpened tip 25 is oriented toward the direction of bending. In this way, the steerable transseptal needle, when in its straight configuration, can be pushed against into the curved region of the introducer, sheath, or guide catheter and not have the sharp point dig into the wall of the introducer, sheath, or guide catheter. The side of the sharpened tip 25 away from the sharp point can further be rounded somewhat to make it even more atraumatic and smooth so it can skate or sled along the curvature of the introducer, sheath, or guide catheter without digging out any material from the wall of the introducer, sheath, or guide catheter.

It is beneficial that the inner tube 2 can sustain compression to generate bending of the outer tube 3 at the distal end back to straight after being curved and even to bend beyond straight in the other (or opposite) direction. In order to sustain compression, it is beneficial that the disconnected side 19 be separated from the connected side 20 at or near substantially the center or midpoint of the tubing. Depending on the width of the slot 17 separating the disconnected side 19 from the connected side 20, the location of the slot can be offset from the midpoint but this is dependent on the wall thickness of the inner tube 2 and the angle of the slotting. In a preferred embodiment, interference exists between the disconnected side 19 and the connected side 20 such that the disconnected side and force transmitting member cannot move substantially inward, a situation that would have negative effects of obstructing the lumen, restricting fluid flow therethrough, trapping stylets or other catheters that need to move longitudinally therein, or buckling sufficiently to prevent application of longitudinal compression forces on the connected side 20.

Figure 12:
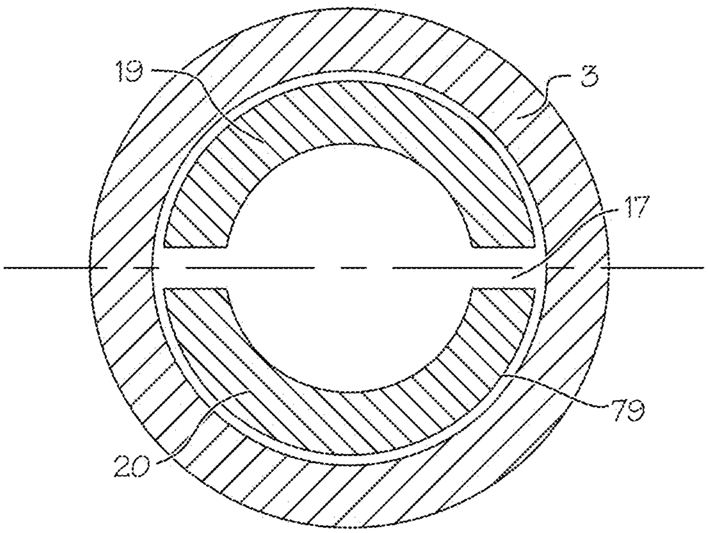
FIG. 12 illustrates a cross-sectional view of a tubing configuration in a steerable transseptal punch within the flexible region, wherein the separation slot in the inner tube is substantially at the midpoint or center of the inner tubing.
Figure 13:
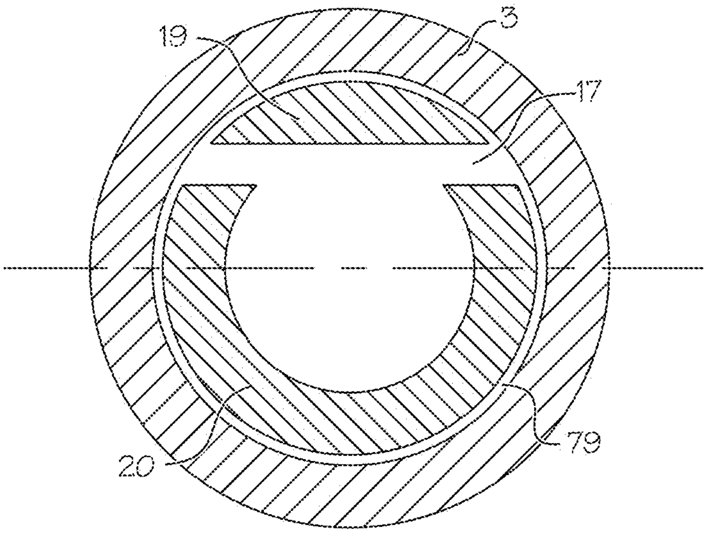
FIG. 13 illustrates a lateral cross-section of a tubing configuration of a steerable transseptal punch within the flexible distal region, with an off-center separation slot.

FIGS. 12 and 13 are cross sections of the inner tube in the split region. FIG. 12 a radial cross-section of an inner tube 2 nested inside an outer tube 3 and separated from the outer tube 2 by a annular, radial gap 78 in the flexible region of an articulating septal punch wherein the inner tube 2 is separated by a split or gap 17 into two approximately or substantially equal parts, a connected side 20 and a disconnected side 19, approximately (or substantially) at the midline or centerline of the cross-section.

FIG. 13 is a radial cross-section of an inner tube 2 nested inside an outer tube 3 and separated from the outer tube 22 by a annular gap 78 in the flexible region of the punch where the inner tube 2 is separated by a split or gap 17 into two substantially unequal parts, a connected side 20 and a disconnected side 19, substantially offset from the midline or centerline of the cross-section.

The disconnected side 19 is retained in close proximity to the outer tube 3 by its stiffness and its inability to deform such that the edges of the disconnected side 19 can pass beyond the edges of the connected side 20 and thus the two sides 20 and 19 are retained radially displaced from centerline. If the gap 17 were too large or either side 20, 19 were small enough to fit within the edges of the other side, then displacement of one side toward the centerline and confounding of the off-center orientation of the connected side 20 or 19 would occur leading to buckling of the connected side 20 in compression and inability to straighten out a bent transseptal needle. Another problem might be loss of torquability and predictability of the direction of bending. Both embodiments shown in FIGS. 12 and 13 maintain circumferential and radial orientation of the inner tube connected side 20 relative to the disconnected side 19 and promote high precision deflection of the distal tip.

In preferred embodiments, the annular gap 78 is minimized and is retained between about 0.0005 to 0.002 inches when the needle is about 0.050 in outside diameter. Furthermore, the split or gap 17 should be as minimal as possible and in preferred embodiments can range from about 0.002 inches to about 0.015 inches with a gap of about 0.004 to 0.010 inches being most preferable.

Figure 14:
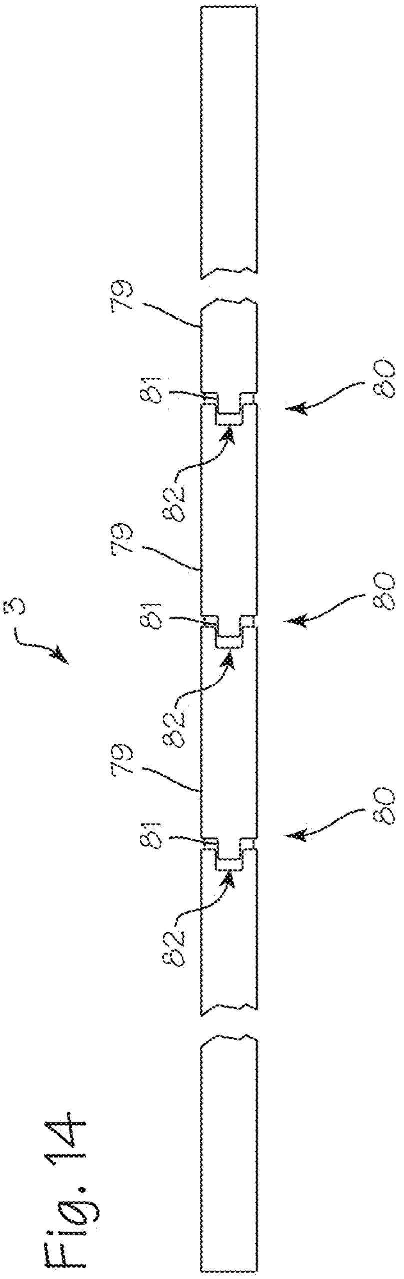
FIG. 14 illustrates a top view of a portion of the distal flexible region of an outer tube comprising dovetails or interlocking grooves to increase torsional resistance to torque or side-to-side motion.
Figure 15:
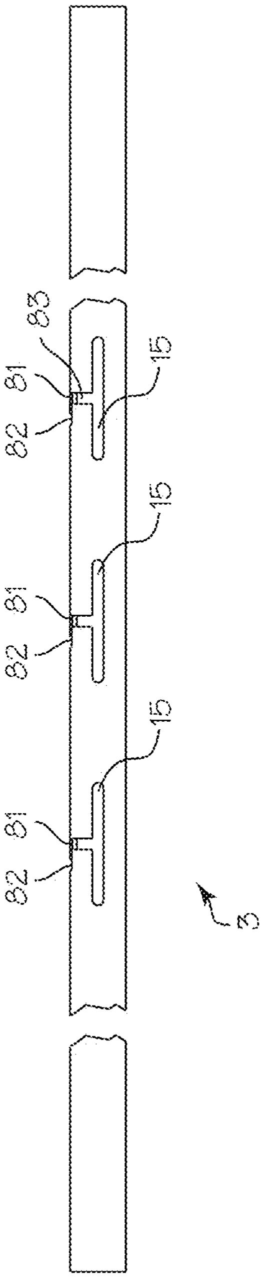
FIG. 15 illustrates a side view of a portion of the distal flexible region of an outer tube comprising dovetails or locking grooves to reduce torsional bending or side-to-side motion.

FIGS. 14 and 15 illustrate alternative embodiments of the outer tube 3. In FIG. 14, the outer tube 3, in the region of the distal, flexible section, comprises a plurality of short longitudinal segments 79 joined by dovetail joints 80 comprising dovetail tails 81 loosely fitted into dovetail gaps 82.

In FIG. 15, which is the same outer tube 3 shown in FIG. 14 viewed from 90° offset from FIG. 14, the outer tube 3 in the region of the dovetail joints, includes the partial lateral slots 83 disposed 90° radially offset from the dovetails and dovetail receivers, joined with the dovetail through circumferential slots 14. The longitudinal T-slots 15 are optional or they can be configured differently.

Figure 16:
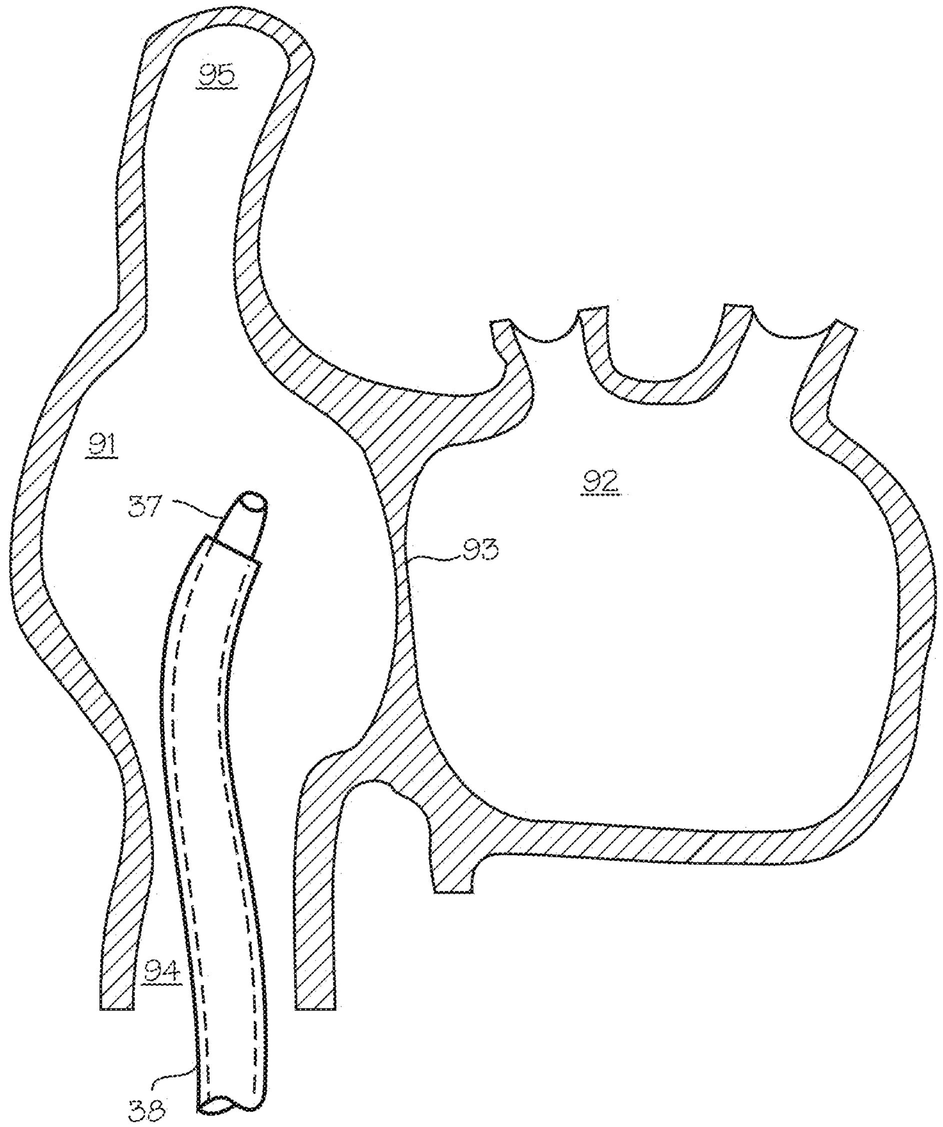
FIGS. 16 through 20 illustrate the use of the steerable transseptal punch in establishing access to the left atrium of the heart from the right atrium.

FIGS. 16 through 20 illustrate the use of the steerable transseptal punch in establishing access to the left atrium of the heart from the right atrium. FIG. 16 a portion of a patient's heart, including the right atrium 91 and left atrium 92 and the fossa ovalis 93 which separates the two, along with the inferior vena cava 94 and superior vena cava 95 initial placement of the distal end of guide catheter 38 and obturator 37 in the right atrium. The distal end of guide catheter is curved to some extent, when disposed within the right atrium, and may be slightly straightened within the confines of the vena cava and right atrium.

Figure 17:
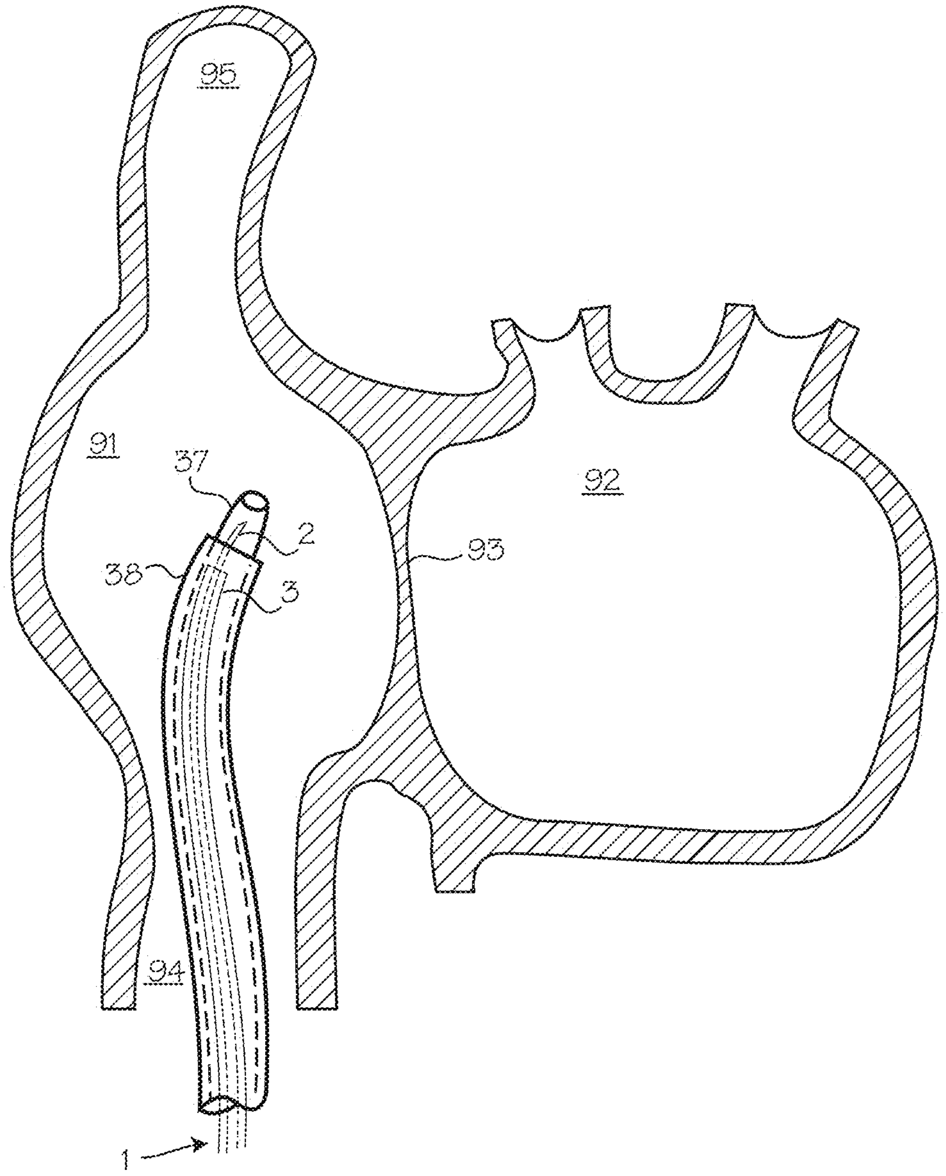
Figure 18:
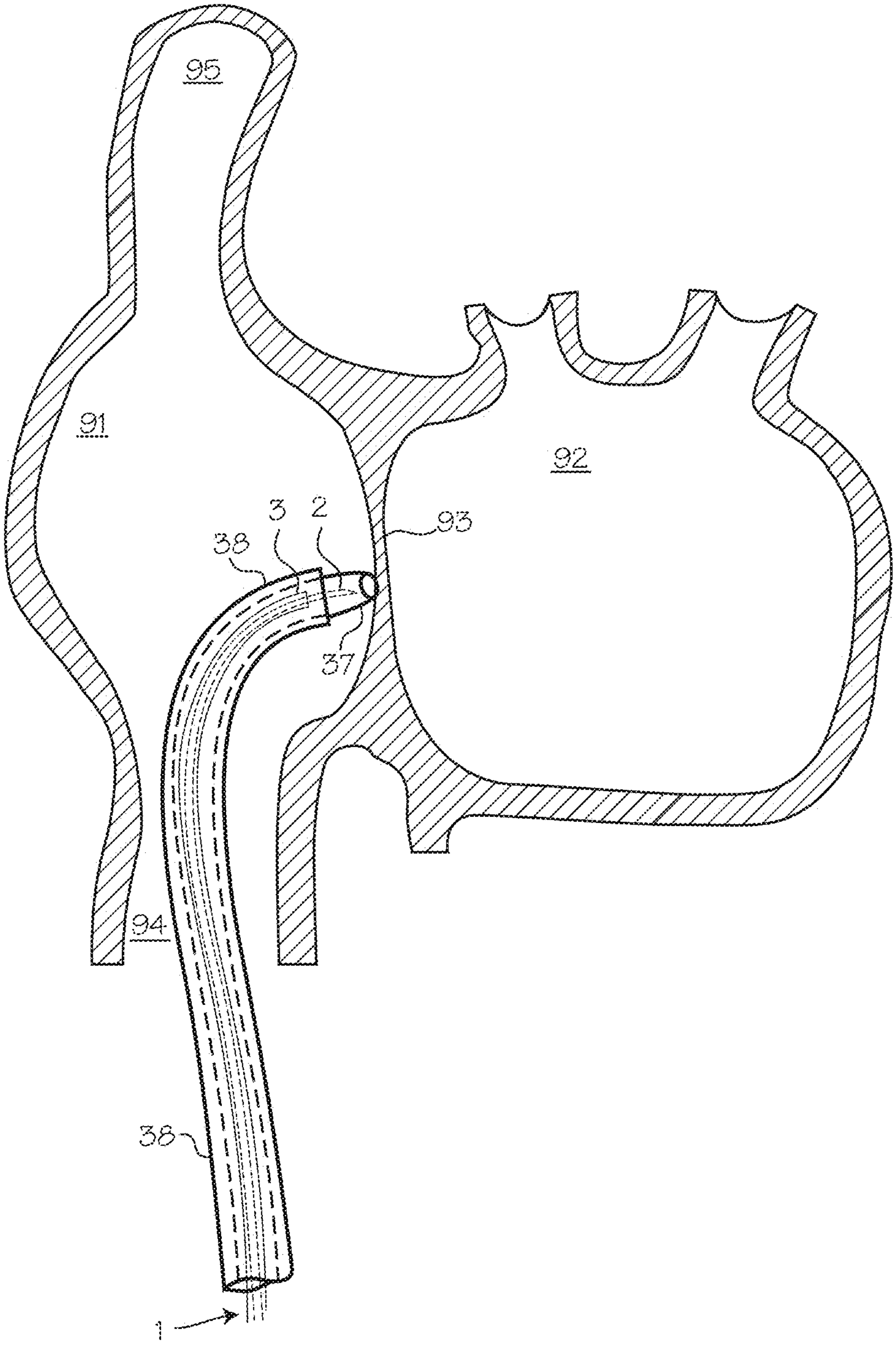
Figure 19:
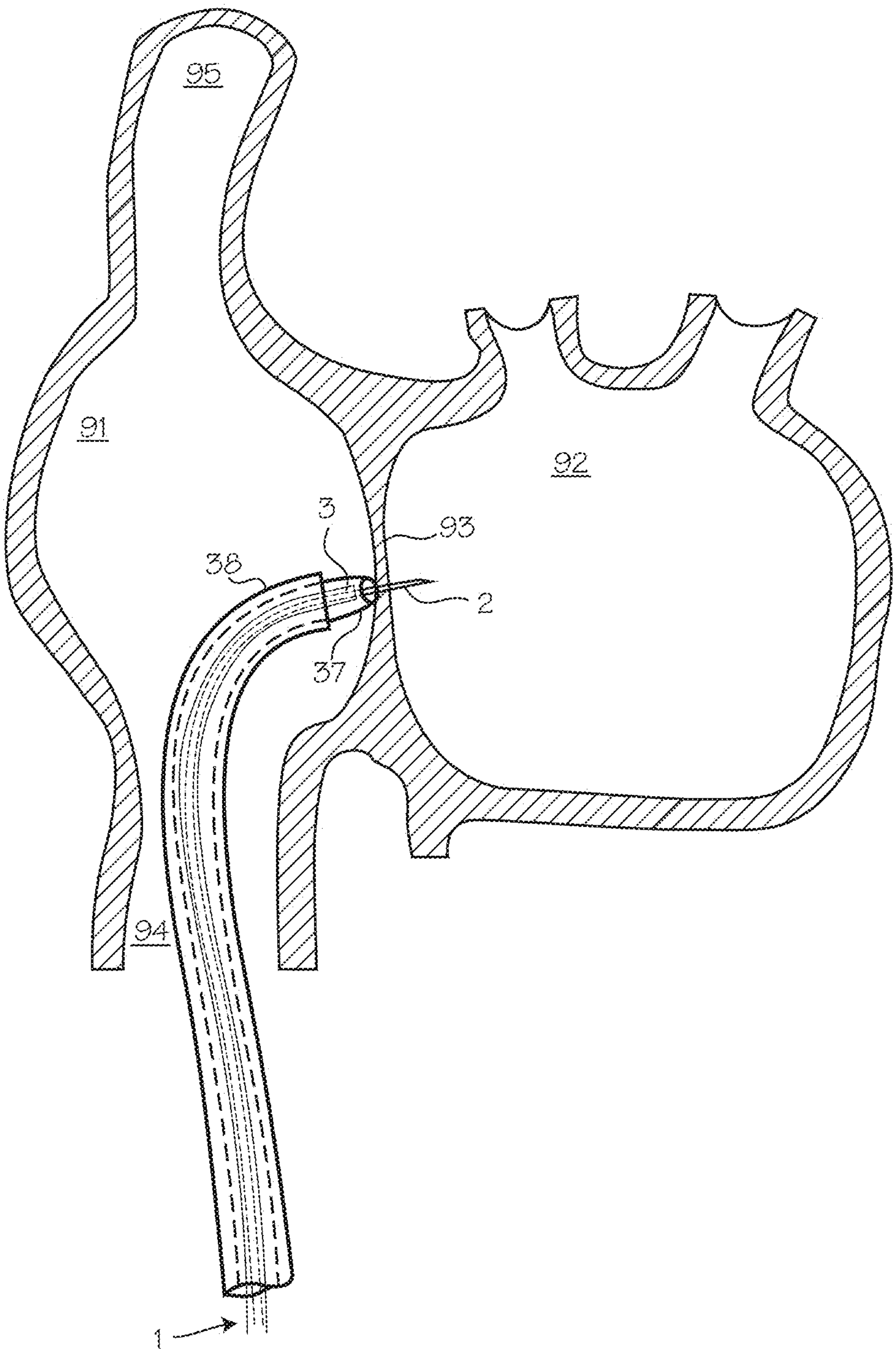
Figure 20:
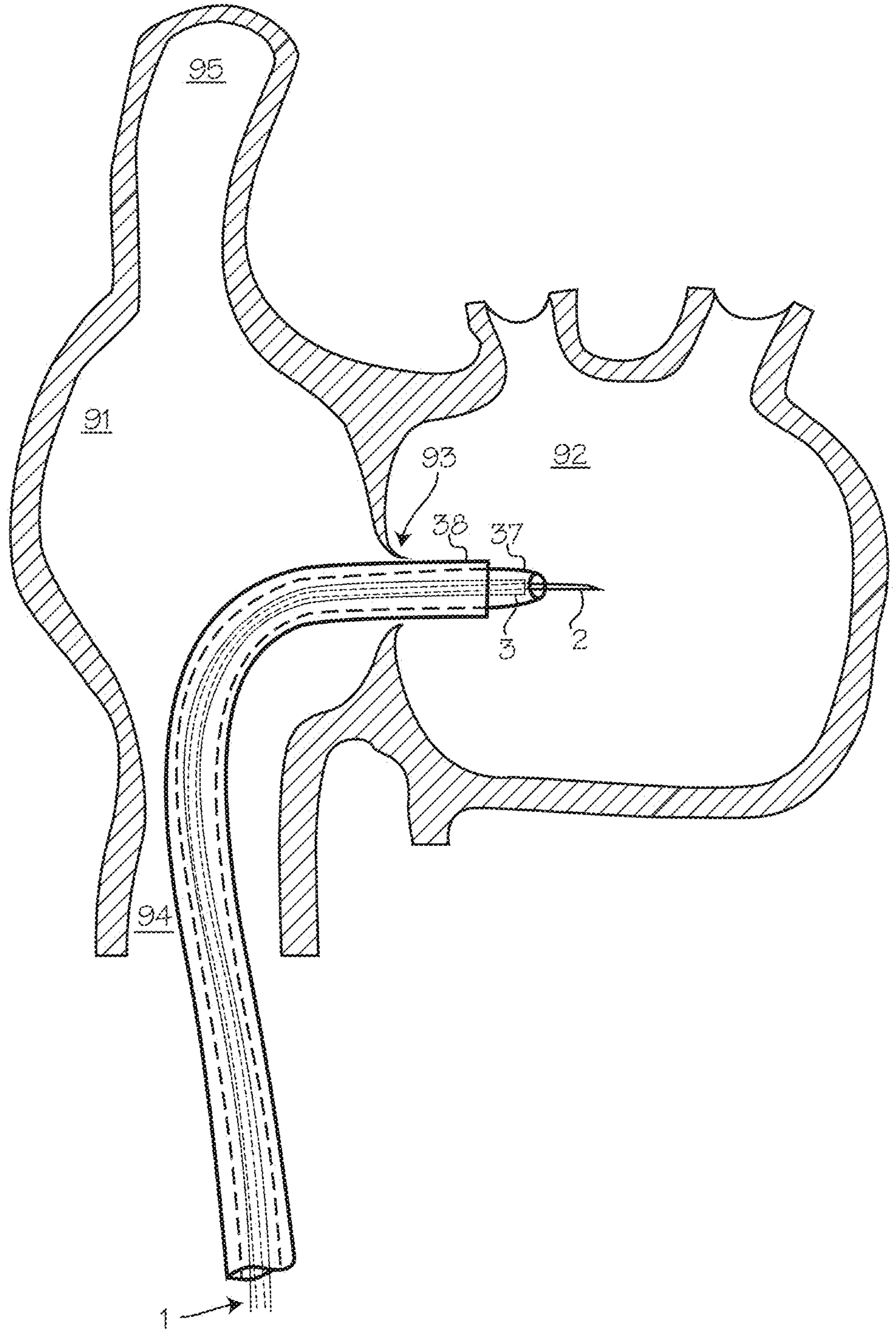

FIG. 17 illustrates the initial insertion of the steerable transseptal punch 1. The punch is pushed through the lumen of the guide catheter 38 or obturator 37 until its distal tip is disposed within the distal end of the guide catheter 38 or obturator 37. During insertion, as the punch is pushed through the guide catheter 38 or obturator 37, the distal end of the punch is deflected by pulling the inner tube 2 relative to the outer tube 3 (or vice versa, or pushing the inner tube relative to the outer tube, or vice versa) to avoid or limit scraping of the sharp tip against the inner wall of the guide catheter 38 or obturator 37. FIG. 18 illustrates the step of bending the distal end of the combined assembly of the guide catheter 38, the obturator 37, and the transseptal punch 1. This is accomplished by bending the tip of the transseptal punch 1, again by pulling the inner tube 2 relative to the outer tube 3 by turning the knob on the proximal hub to push the outer tube 3 distally over the inner tube 2. Deflection of the transseptal punch 1 will force deflection of the guide catheter 38 (and obturator 37) as well. As illustrated, the distal tip of the assembly is bent, and the assembly is rotated, to place the tip and the outlet of the lumen of the guide catheter 38 in apposition to the fossa ovalis. At this point, as shown in FIG. 19, the transseptal punch is pushed distally, relative to the guide catheter 38, to force the sharp tip out of the distal end of guide catheter 38 and/or obturator 37 and through the fossa ovalis. Finally, as shown in FIG. 20, the guide catheter 38 and/or obturator 37 is pushed through the puncture created by the punch 1, so that the distal tip of the guide catheter 38 is disposed within the left atrium 92. The transseptal punch 1 (and obturator 37, if still in place) may now be withdrawn proximally and removed from the guide catheter 38. The empty lumen of the guide catheter 38 can now be used to pass any desired working catheter into the left atrium.

Thus, the method of described in FIGS. 16 through 20 entails punching a hole in a body lumen or hollow organ wall entails a surgeon (or cardiologist) performing the preliminary steps of (1) inserting a guidewire into a patient's body lumen and routing the guidewire to a location near a target site wherein the target site is an organ or body lumen wall (the fossa ovalis, for example) and (2) advancing a guide catheter over the guidewire to the target site, wherein the guide catheter is an axially elongate structure having a proximal end, a distal end, and a lumen extending therethrough, and (3) removing the guidewire from the guide catheter. Next, the surgeon, (4) using an axially elongate punch as described in FIGS. 1 through 15, comprising an integral deflecting mechanism comprising deflectable region at the distal end of the punch which itself comprises an inner tube with a longitudinally slotted region and an outer tube with a snake cut region disposed over the longitudinally slotted, and means for tensioning or compressing the inner tube relative to the outer tube, inserts the punch into the lumen of the guide catheter and routes the punch to the target site, wherein the punch is substantially straight and uncurved and optionally deflecting the deflectable region as desired to negotiate any curves in the guide catheter. With the deflectable region disposed within the distal end of the guide catheter, the surgeon deflects, with the integral deflecting mechanism, the deflectable near the distal end of the punch so that the punch and surrounding guide catheter are substantially curved at the distal end and oriented toward and against the target site. This step is performed after completing the step of inserting the axially elongate punch into the guide catheter and routing the punch to the target site. Next, the surgeon or cardiologist advances the tip of the punch from the distal end of the guide catheter and punches a hole in the body lumen or hollow organ wall with the punch, and advances the punch through the body lumen or hollow organ wall. Finally, the surgeon or cardiologist removes the punch and the integral deflecting mechanism from the guide catheter.

The steering mechanism disclosed herein, comprising two or more nested axially elongate cylindrical tubes moving relative to each other only along the longitudinal axis, can provide a high degree of precision, repeatability, force, column strength, torsional control, and the like, in a configuration with extremely thin walls and large inside diameter (ID) to outside diameter (OD) ratio. One of the tubes comprises partial lateral cuts or complex lateral gaps and the other tube comprising a split running substantially the length of the flexible region. The disconnected side of the slit tube can be removed so that only a partially formed, connected side remains. However, in preferred embodiments, the disconnected side, which is actually retained at the distal end, is not removed but serves to fill space within the lumen of the outer tube 3 to prevent kinking, improve column strength, prevent lumen collapse and provide for guiding of central stylets or catheters. Prior art pull-wire steering devices require greater wall thickness, which reduces the size of the internal lumen relative to a given outside diameter, or they do not have the same degree of precise movement at the distal tip under control from the proximal end of the device.

However, the transseptal punch disclosed above, with the slit inner tube and snake cut outer tube, can maintain its structure in compression and provide precise control, and maintain a central lumen larger than any other type of steerable transseptal punch. The resistance to buckling occurs even when the inner tube is slotted longitudinally because the inner tube is constrained within the outer tube using very tight tolerances that will not let the inner tube bend out of its straight orientation, even under compression.

The punch can be used to create holes in various structures in the body. It is primarily configured to serve as an articulating or variable deflection Brockenbrough needle, for use in puncturing the fossa ovalis to gain access to the left atrium from the right atrium. However, the steerable punch can be used for applications such as transluminal vessel anastomosis, biopsy retrieval, or creation of holes in hollow organs or lumen walls. The punch can be used in the cardio-vascular system, the pulmonary system, the gastro-intestinal system, or any other system comprising tubular lumens, where minimally invasive access is beneficial. The punch can be configured to be coring or non-coring in operation, depending on the shape of the distal end and whether an obturator or the circular hollow end of the punch is used to perform the punching operation. The punch facilitates completion of transseptal procedures, simplifies routing of the catheters, minimizes the chance of embolic debris being dislodged into the patient, and improves the ability of the cardiologist to orient the punch for completion of the procedure.

As used in the description of the transseptal punch, the terms proximal and distal are used as they are used in the art of medical devices. The term proximal refers to locations along the long axis of the device closer to the user, the handle and the insertion point for the device. The term distal refers to point further from the user, the handle and insertion point. The distal and proximal ends of the catheter may or may not coincide with the distal and proximal portions of the patient's vasculature, where, for example, the transseptal punch is inserted into a vein in the leg, which is distal to the heart, (the heart, being the origin of the vasculature, is proximal to the remainder of the vasculature).

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A transseptal punch comprising:

an outer tube characterized by a proximal end, a distal end, and a first flexible region at the distal end of the outer tube, said first flexible region characterized by a proximal and a distal end, said first flexible region being more flexible than a proximal region of the outer tube; and an inner tube characterized by a proximal and a distal end, said inner tube having a second flexible region near said distal end of the inner tube, said second flexible region being more flexible than a proximal region of the inner tube, and a distal tip adapted to pierce body tissue;

said inner tube being disposed within the outer tube, extending from the proximal end of the outer tube to the distal end of the outer tube, and terminating distally in the distal tip disposed distally beyond the distal end of the outer tube, said inner tube fixed to the outer tube at a point in the outer tube proximate the distal end of the first flexible region of the outer tube; and a source of radiofrequency energy operably connected to the inner tube to apply RF energy to the distal tip.

2. A method of accessing the left atrium of the heart of a patient, from the right atrium and through the fossa ovalis of the heart, said method comprising the steps of:

providing a punch for punching a hole in the fossa ovalis, said punch characterized by a distal end and a proximal end, said punch comprising:

an outer tube characterized by a proximal end, a distal end, and a first flexible region at the distal end of the outer tube, said first flexible region characterized by a proximal and a distal end, said first flexible region being more flexible than a proximal region of the outer tube; and an inner tube characterized by a proximal and a distal end, said inner tube having a second flexible region near said distal end of the inner tube, said second flexible region being more flexible than a proximal region of the inner tube, and a distal tip adapted to pierce body tissue;

said inner tube being disposed within the outer tube, extending from the proximal end of the outer tube to the distal end of the outer tube, and terminating distally in the distal tip disposed distally beyond the distal end of the outer tube, said inner tube fixed to the outer tube at a point in the outer tube proximate the distal end of the first flexible region of the outer tube; and navigating the punch through a guide catheter until the distal tip of the inner tube is in contact with the fossa ovalis; and connecting a source of radiofrequency energy to the inner tube and applying radiofrequency to the distal tip.

* * * * *